(12) United States Patent
Lee

(10) Patent No.: US 7,170,302 B2
(45) Date of Patent: Jan. 30, 2007

(54) CAPACITIVE SOIL MOISTURE SENSOR

(76) Inventor: Fu Ching Lee, 351 W. Martin Luther King, Jr. Blvd., Los Angeles, CA (US) 90037

( * ) Notice: Subject to any disclaimer, the term of this patent is extended or adjusted under 35 U.S.C. 154(b) by 0 days.

(21) Appl. No.: 11/133,023

(22) Filed: Jun. 27, 2005

(65) Prior Publication Data

US 2006/0290360 A1 Dec. 28, 2006

(51) Int. Cl.
*G01R 27/26* (2006.01)
(52) U.S. Cl. ............ 324/690; 324/664; 324/689
(58) Field of Classification Search ............ 324/690, 324/664
See application file for complete search history.

(56) References Cited

U.S. PATENT DOCUMENTS

| 3,710,244 A | * | 1/1973 | Rauchwerger | ............ 324/664 |
| 4,796,654 A | | 1/1989 | Simpson | |
| 4,837,499 A | | 6/1989 | Scherer, III | |
| 4,850,386 A | * | 7/1989 | Bireley | ............ 324/689 |
| 4,929,885 A | * | 5/1990 | Dishman | ............ 324/690 |
| 5,418,466 A | * | 5/1995 | Watson et al. | ............ 324/668 |
| 5,424,649 A | | 6/1995 | Gluck et al. | |
| 5,479,104 A | | 12/1995 | Cambell | |
| 5,858,536 A | | 1/1999 | Yanagisawa | |
| 5,859,536 A | * | 1/1999 | Stockton | ............ 324/690 |
| 6,147,504 A | | 11/2000 | Schmidt | |
| 6,756,793 B2 | | 6/2004 | Hirono et al. | |
| 6,842,018 B2 | * | 1/2005 | McIntosh | ............ 324/664 |

\* cited by examiner

*Primary Examiner*—Andrew H. Hirshfeld
*Assistant Examiner*—Timothy J. Dole

(57) ABSTRACT

A capacitive soil moisture sensor that is easy to install, does not require complex calibration, can sense moisture at a particular depth, can accommodate soils of different composition, does not alter soil densities, provides fast response to changes in moisture and provides stable long term use. The sensor comprising of a body (10) onto which is attached a plurality of first electrode (20) and a plurality of second electrode (30). A plurality of protective layer (50) of low dielectric constant material is applied over the electrodes and against the body (10) to provide a physical barrier to prevent a conduction path from the first electrode (20) to the second electrode (30) and to provide protection against physical damage. The first and second electrodes (20), (30), once inserted into the soil, forms a capacitor with the soil as the dielectric. A change in soil moisture causes the capacitance of the sensor to change.

4 Claims, 4 Drawing Sheets

CAPACITIVE SOIL MOISTURE SENSOR

CROSS-REFERENCE TO RELATED APPLICATION

Not Applicable

FEDERALLY SPONSORED RESEARCH

Not Applicable

SEQUENCE LISTING OR PROGRAM

Not Applicable

FIELD OF INVENTION

The present invention relates to a soil moisture sensor and more particularly, to a soil moisture sensor that measures the moisture of an area of soil at a particular depth.

BACKGROUND OF INVENTION

In the field of irrigation it is necessary to ensure that water is properly controlled and supplied to vegetation. Some plant matter suffers in an abundance of water and others in a lack of. To this end, it is important to be able to determine the water content of the supporting soil particularly in the regions proximate to the vegetation's major root structures.

Many examples of sensors are detailed in prior art and can be loosely group into the following:

Resistive/conductive sensors. U.S. Pat. No. 4,796,654 is an example. These type of sensors rely on the resistive/conductive property of moist soils and consist of at least two electrodes inserted into the soil and a means to measure the resistance/conductance between these electrodes. The resistive/conductive property of soils changes with its composition. Property such as salinity and acidity greatly affects resistive/conductive readings and for this type of sensor to be effective, a comparative method is required to calibrate the sensor to the soil. These types of sensors were therefore difficult to install and maintain.

Known dielectric sensors. U.S. Pat. No. 4,837,499 is an example. These type of sensors consist of a know material that is sandwiched between at least two plates electrodes. The material becomes the dielectric of the sensor. The sensor is place in contact with the soil to be measured and by contact the dielectric material becomes moist. The capacitance or resistance of the resultant sensor is measured. These types of sensors provided immunity to the composition of the soil but suffer from a limited useful life since the dielectric material degrades with time. Additionally these sensors suffer from slow response since the dielectric material takes time to reach the same moisture level as the surrounding soil.

Capacitive sensors. U.S. Pat. No. 5,859,536 is an example. These types of sensor consist of at least two electrodes separated by the soil to be measured. The capacitance of the resultant capacitor is measured. These sensors provide immunity to the composition of the soil, however, with these sensors it is difficult to determine the wetness at a particular depth. To achieve this the user has to excavate and bury the sensor at the desired depth. This causes the density of the soil to change and therefore the measured wetness is not a true representation of the original soil sample.

Other available sensors are generally not suitable for the layman and or require expensive measuring equipment.

OBJECTS AND ADVANTAGES

Accordingly, several objects and advantages of my invention are:
(a) easy to install;
(b) does not require complex calibration;
(c) can sense moisture at a particular depth;
(d) can accommodate soils of different composition;
(e) does not alter soil densities;
(f) provides fast response to changes in moisture; and
(g) provides stable long term use.

Still further objects and advantages will become apparent from consideration of the ensuing description and drawings.

SUMMARY OF THE INVENTION

In accordance with the above-mentioned objects and advantages, the present invention consists of a capacitive sensor for determining the moisture content of a region of soil at a particular depth. The sensor comprising of a body onto which is attached a plurality of first electrode and a plurality of second electrode. A plurality of layers of low dielectric constant material is applied over the electrodes and against the body to provide a physical barrier to prevent a conduction path from the first electrode to the second electrode and to provide protection against physical damage. The first and second electrodes, once inserted into the soil, form a capacitor with the soil as the dielectric. A change in soil moisture causes the capacitance of the sensor to change.

DRAWINGS

DETAILED DESCRIPTION

Figure 1:
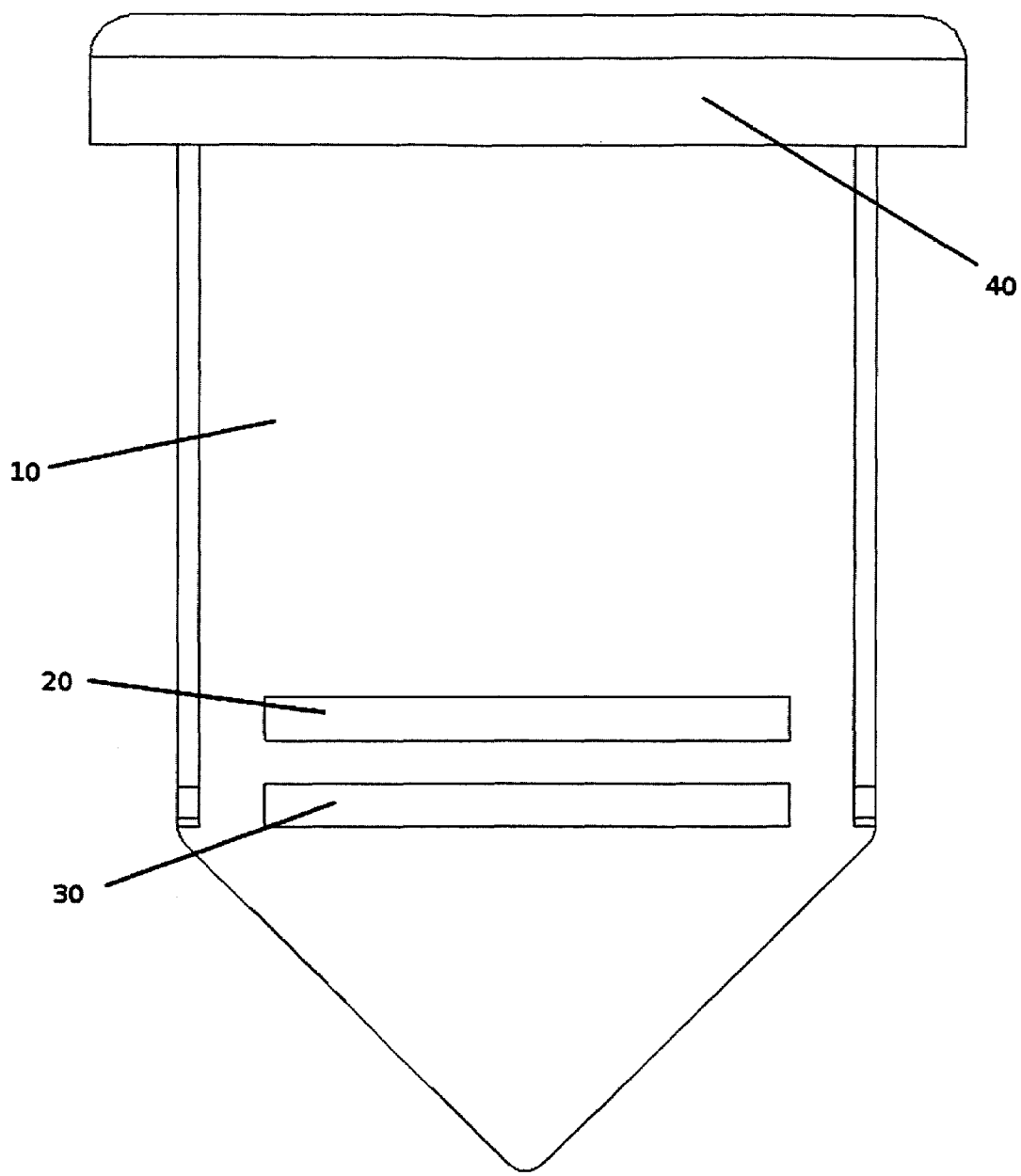
FIG. 1 is a front view of a preferred embodiment of the present invention.
Figure 2:
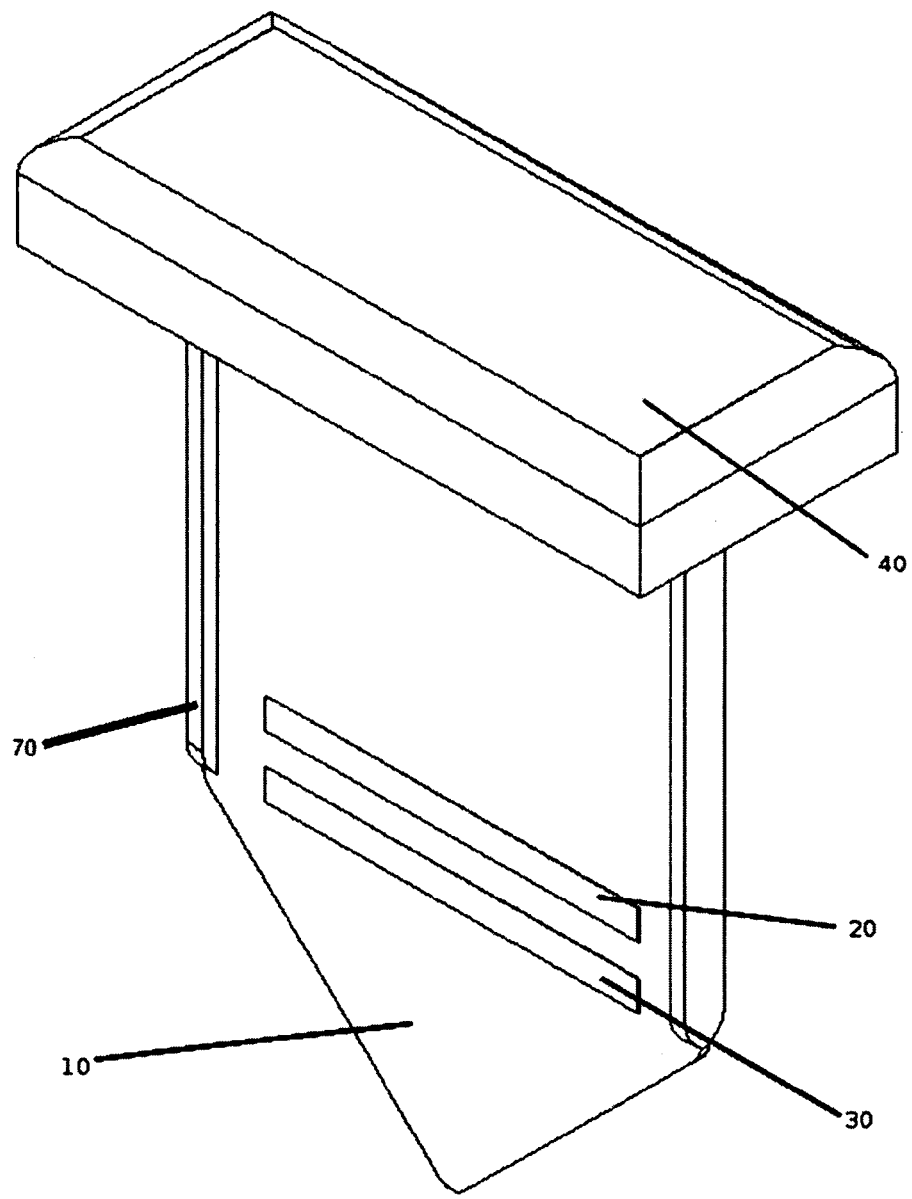
FIG. 2 is a perspective view of a preferred embodiment of the present invention.

The preferred embodiment of the present invention, as shown in FIG. 1 and FIG. 2, comprises of a body 10 which is made of a corrosion resistant and ultra-violet light resistant material such as fiber glass, polyurethane, ABS or similar. Body 10 is formed into a flat and thin sheet to allow easy insertion into the soil. Additional rib structures 70 to act as stiffeners can be form as part of body 10 to prevent twisting and bending during the insertion process.

A plurality of conductive material is attached to body 10 to form a first electrode 20. A plurality of conductive material is similarly attached to body 10 to form a second electrode 30. The conductive material of first electrode 20 and second electrode 30 are preferably corrosive resistant metals such as gold or platinum, however due to the cost of such metals, other materials such as copper, bronze, zinc, nickel or similar can be used. Additionally conductive resins can be used in place of the metals.

Figure 4:
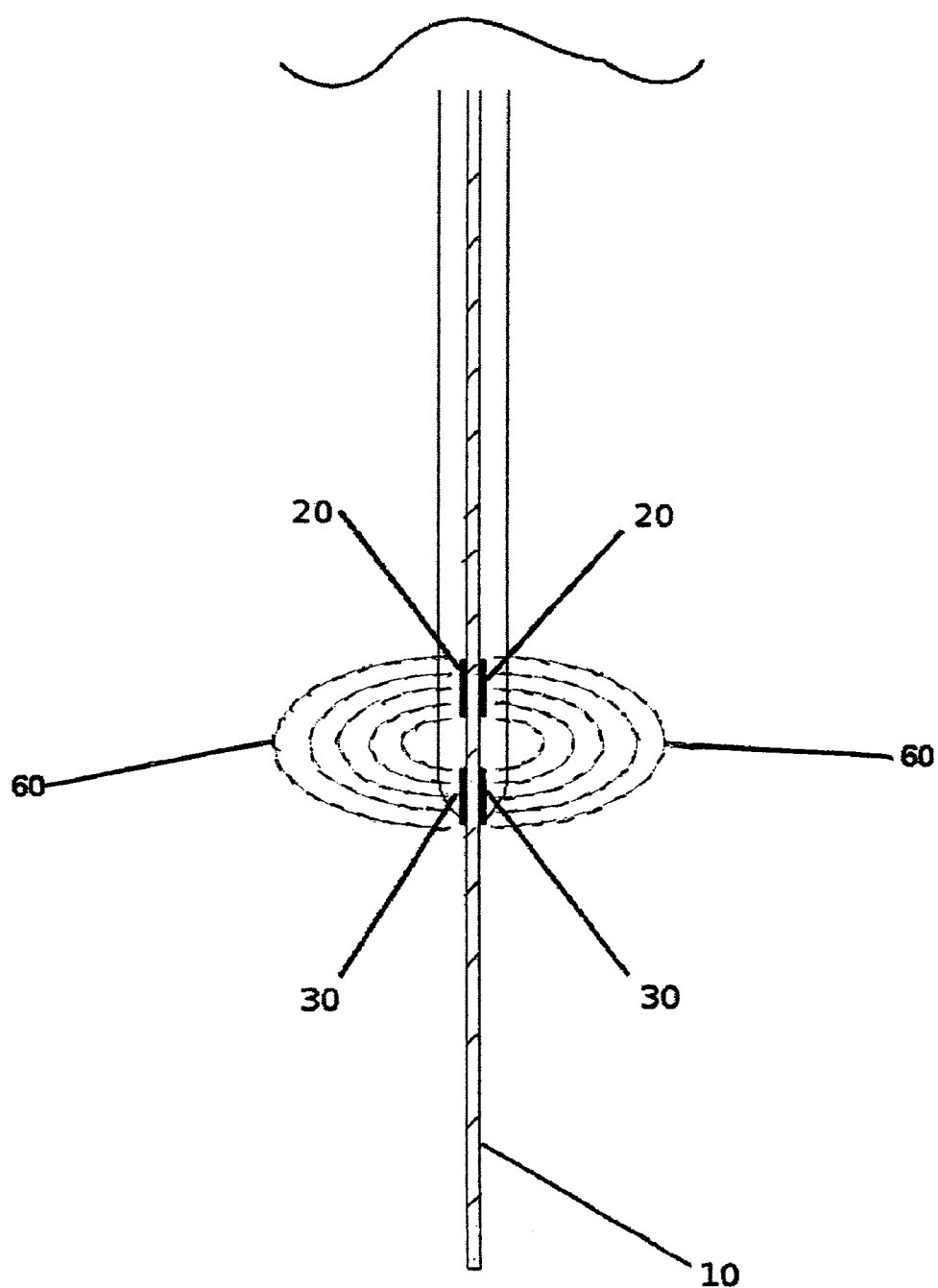
FIG. 4 is a detailed side cut-away view of a preferred embodiment of the present invention.

FIG. 4 shows a representation of the electrical field path 60 of the sensor when an alternating electric potential is applied between the electrodes 20 and 30. The first electrode 20 and second electrode 30 are preferably formed such that the majority of the electrical field path travels perpendicular to the expose face of the electrodes 20 and 30 and not parallel to the expose face. This can be achieved by ensuring that the first electrode 20 and second electrode 30 are formed such that they are thinner than they are wide.

Figure 3:
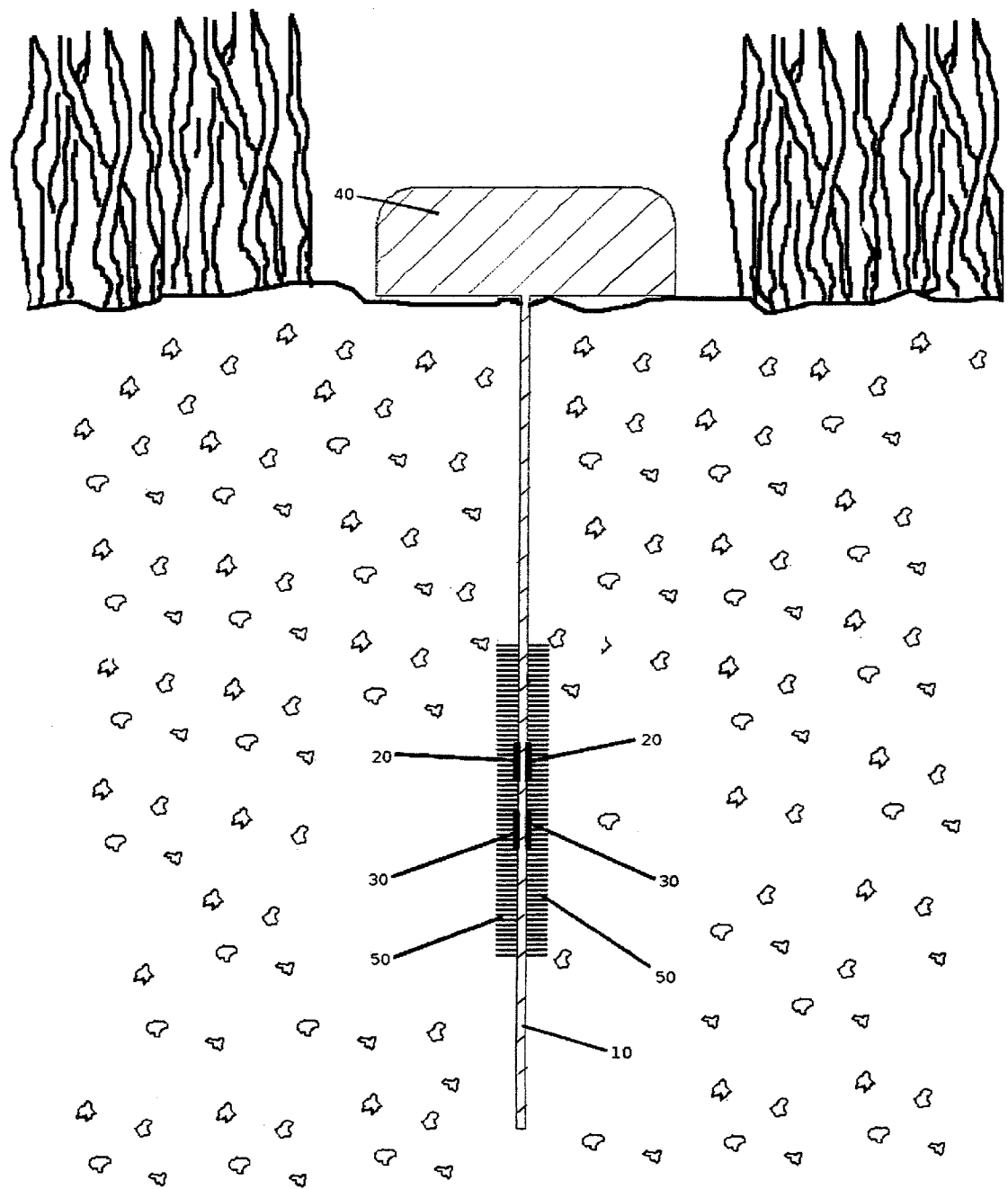
FIG. 3 is a side cut-away view of a preferred embodiment of the present invention in a sample application.

To protect the first electrode 20 and second electrode 30 a plurality of protective layer 50 comprising a corrosion resistant and abrasive resistant material is attached to the body 10 over the first and second electrodes 20, 30. FIG. 3 shows a representation of the protective layer 50. The protective layer 50 preferably should have a low dielectric constant relative to water to reduce its effect on the overall capacitance of the sensor. Suitable materials include fluoropolymers, chloropolymers, chlorofluoropolymers, polyparaxylene or similar.

The header 40 is formed and attached to the body 10 or can be a part of the body 10. The header 40 serves several purposes. The primary being to prevent channeling of free water from rain or irrigation directly down to the face of the electrodes. Additionally it provides a handy place to exert pressure on the sensor during the insertion process; it provides a positive stop to insertion; and can be used to house electronic circuity.

In operation, the sensor is inserted into the soil. The first electrode 20 and second electrode 30 forms two plates of a capacitor with the soil immediately surrounding the electrodes forming the dielectric. Suitable measuring equipment is attached and provides a reading of the capacitance of the capacitor so formed. Since the geometry and composition of the electrodes are fixed at manufacture, changes in capacitance of the sensor is due to changes in the dielectric material or in this case the soil, hence a direct relationship between capacitance of the sensor and the wetness of the soil.

CONCLUSION, RAMIFICATION AND SCOPE OF INVENTION

Thus, the reader will see that the capacitive soil moisture sensor of the invention provides an economical device. Furthermore, the sensor has the additional advantage in that it:

is easy to install;
does not require complex calibration;
can sense moisture at a particular depth;
can accommodate soils of different composition;
does not alter soil densities;
provides fast response to changes in moisture; and
provides stable long term use.

While my above description contains much specificity, these should not be construed as limitations on the scope of the invention, but rather as an exemplification of one preferred embodiment thereof. Many other variations are possible.

Accordingly, the scope of the invention should be determined not by the embodiment illustrated, but by the appended claims and their legal equivalent.

The invention claimed is:

1. A capacitive soil moisture sensor having a lower portion adapted to be inserted into the earth comprising of:
    a sensor carrier comprising;
        a body having a generally spade shaped with one tapered end, one opposite flat end and two parallel sides, said body being of a thin structurally rigid material with a plurality of narrow ribs parallel to said two parallel sides,
        a header enclosure having a generally rectangular box shaped with one top face, one opposite bottom face,
        said header being joined at said bottom face to said body at said flat end such that said header's said bottom face is perpendicular to said body and such that said bottom face over-hangs said body generally equal distance on all sides,
    a first electrode comprising a plurality of sheets of conductive material,
    a second electrode comprising a plurality of sheets of conductive material,
    a protective layer comprising of a plurality of corrosion resistant and
    abrasive resistant material,
    said first electrode being joined onto the surface of one face of said sensor carrier's said body,
    said second electrode being joined onto the surface of said face of said sensor carrier's said body in the same orientation and alignment as said first electrode, said first electrode and said second electrode positioned so they do not touch, said protective layer joined onto the surface of said face of said sensor carrier's said body over said first electrode and said second electrode,
    said first electrode and said second electrode so positioned on said sensor carrier to be inserted into the earth so forms a planar capacitor with soil as dielectric.

2. The capacitive soil moisture sensor of claim 1 in which the sensor carrier consist of a corrosion resistant and ultraviolet light resistant material said material selected from fiber glass, polyurethane, and ABS.

3. The capacitive soil moisture sensor of claim 1 in which the protective layer consists of a low dielectric constant material relative to water said material selected from fluoropolymers, chloropolymers, chlorofluoropolymers, and polyparaxylene.

4. The capacitive soil moisture sensor of claim 1 in which the first electrode consist of a conductive material said conductive material selected from gold, platinum, copper, bronze, zinc, and nickel.

* * * * *